United States Patent
Ma et al.

(10) Patent No.: US 9,880,409 B2
(45) Date of Patent: Jan. 30, 2018

(54) FLAT-PANEL PRODUCT INSPECTION DEVICE

(71) Applicants: BOE TECHNOLOGY GROUP CO., LTD., Beijing (CN); BEIJING BOE DISPLAY TECHNOLOGY CO., LTD., Beijing (CN)

(72) Inventors: Hongtao Ma, Beijing (CN); Wei Zhao, Beijing (CN); Lizhu Yu, Beijing (CN); Jinping Zhou, Beijing (CN); Guodong Wang, Beijing (CN); Xiaolong Tian, Beijing (CN)

(73) Assignees: BOE TECHNOLOGY GROUP CO., LTD., Beijing (CN); BEIJING BOE DISPLAY TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/236,762

(22) Filed: Aug. 15, 2016

(65) Prior Publication Data
US 2017/0255037 A1    Sep. 7, 2017

(30) Foreign Application Priority Data
Mar. 7, 2016    (CN) .......................... 2016 1 0127825

(51) Int. Cl.
| | |
|---|---|
| *G01N 21/01* | (2006.01) |
| *G02F 1/13* | (2006.01) |
| *G01N 21/95* | (2006.01) |
| *G01N 21/88* | (2006.01) |
| *G01N 21/13* | (2006.01) |

(52) U.S. Cl.
CPC .......... *G02F 1/1309* (2013.01); *G01N 21/13* (2013.01); *G01N 21/8806* (2013.01); *G01N 21/95* (2013.01); *G01N 2021/9513* (2013.01)

(58) Field of Classification Search
CPC .. G02F 1/1309; G01N 21/13; G01N 21/8806; G01N 21/95; G01N 2021/9513
USPC ......................................... 356/244, 426–428
See application file for complete search history.

(56) References Cited

U.S. PATENT DOCUMENTS

| | | | |
|---|---|---|---|
| 6,628,380 B1 * | 9/2003 | Fujimori | G01N 21/8806 356/237.1 |
| 2004/0001177 A1 * | 1/2004 | Byun | G02F 1/1339 349/187 |

* cited by examiner

*Primary Examiner* — Tri T Ton
(74) *Attorney, Agent, or Firm* — Nath, Goldberg & Meyer; Joshua B. Goldberg

(57) ABSTRACT

The invention discloses a flat-panel product inspection device, comprising: a horizontal conveying mechanism for driving a flat-panel product in a horizontal state to move in a first horizontal direction; a guiding clamp for clamping the flat-panel product when the flat-panel product is moved to a first position; and a turnover mechanism connected with the guiding clamp and used to drive the guiding clamp to turn around a first rotating axis after the flat-panel product is clamped by the guiding clamp, so that the flat-panel product is turned from the horizontal state to a vertical state, the first rotating axis being parallel to the first horizontal direction.

15 Claims, 5 Drawing Sheets

FLAT-PANEL PRODUCT INSPECTION DEVICE

CROSS-REFERENCE TO RELATED APPLICATION

This application claims the priority of Chinese Patent Application No. 201610127825.9 submitted to the Chinese Intellectual Property Office on Mar. 7, 2016, the disclosure of which is incorporated herein in its entirety by reference.

TECHNICAL FIELD

The invention relates to the field of plate-shaped product inspection technology, and more particularly, to a flat-panel product inspection device.

BACKGROUND OF THE INVENTION

Currently, Thin Film Transistor-Liquid Crystal Display (TFT-LCD) has become the mainstream flat-panel display, which substantially comprises components such as colour film substrate, liquid crystal layer, array substrate and polarizer, wherein polarizer has a significant impact on the optical properties of LCD such as brightness, contrast and angle of visibility, the visual defects (appearance defects) of which may directly lead to an unqualified LCD. Appearance defects of the polarizer are varied in types and causes and can be divided into substrate defects, adhesive surface defects, protective film defects and the like according to the location thereof; and divided into foreign matters, scratches, creases, dints, bubbles and the like according to the appearance characteristics thereof.

Currently, researches are focused on optical performance detection technology of the polarizer, and artificial visual inspection is still widely used in the inspection of appearance defects. FIG. 1 is a structural schematic diagram of a polarizer visual inspection device in the prior art. As shown in FIG. 1, the polarizer visual inspection device comprises a horizontal transmission belt 7 which is disposed at a tip end of a polarizer attaching device and through which a to-be-inspected display panel 6 is conveyed to the next process position after the polarizer is attached thereon. During this process, an inspector can directly pick up the to-be-inspected display panel 6 from the horizontal transmission belt 7, and then inspect the polarizer on both sides of the to-be-inspected display panel 6.

However, during practical operation, the to-be-inspected display panel 6 is prone to be damaged when the inspector wearing rubber gloves picks and places the product from/onto the device. In addition, the external environment may also affect the product yield. Further, when large-size display panels are inspected, since the display panels are large in size and thin in thickness, it is difficult to perform manual operation, thereby prolonging operation and inspection time, and thus reducing production efficiency.

FIG. 2 is a schematic diagram of another polarizer inspection device in the prior art. As shown in FIG. 2, in order to solve the above problems, a manipulator 8 is provided on a side of the horizontal transmission belt by manufacturers; the front end of the manipulator 8 is provided with a suction cup with a plurality of suction holes 9 arranged thereon. When defect inspection is performed on the polarizer, the to-be-inspected display panel 6 on the horizontal transmission belt 7 is sucked up via the suction cup and rotated to a vertical state by the manipulator 8 for inspectors to inspect.

In practical operation, when an adsorption force between the suction cup and the to-be-inspected display panel is too small, a problem of the to-be-inspected display panel dropping off may occur; when the adsorption force between the suction cup and the to-be-inspected display panel is too large, it may cause the to-be-inspected display panel to deform to appear mura, thereby affecting inspection.

In view of the above, providing a safe and efficient flat-panel product inspection device has become an urgent technical problem to be solved in the art.

SUMMARY

An object of the invention is to provide a flat-panel product inspection device which can help inspectors perform a safe and efficient inspection on flat-panel products.

To this end, according to one aspect of the invention, there is provided a flat-panel product inspection device comprising:

a horizontal conveying mechanism for driving a flat-panel product in a horizontal state to move in a first horizontal direction;

a guiding clamp for clamping the flat-panel product when the flat-panel product is moved to a first position; and a turnover mechanism connected with the guiding clamp and used to drive the guiding clamp to turn around a first rotating axis after the flat-panel product is clamped by the guiding clamp, so that the flat-panel product is turned from the horizontal state to a vertical state, the first rotating axis being parallel to the first horizontal direction.

The guiding clamp may comprise an upper clamp portion, a lower clamp portion and a connection portion connected with the upper clamp portion and the lower clamp portion, and the upper clamp portion and the lower clamp portion are provided to be parallel to each other; and the connection portion is used to drive the upper clamp portion and the lower clamp portion to move toward or away from each other in a vertical direction.

The upper clamp portion may comprise a first connection plate and a plurality of first support plates which are sequentially arranged in the first horizontal direction, and all of the first support plates are parallel to each other and extend along a second horizontal direction; and the lower clamp portion may comprise a second connection plate and a plurality of second support plates which are sequentially arranged in the first horizontal direction, and all of the second support plates are parallel to each other and extend along the second horizontal direction.

A side of the first support plate may be provided with a plurality of first rollers that are connected with the first support plate via a first rolling shaft which is parallel to the first horizontal direction; and A side of the second support plate may be provided with a plurality of second rollers that are connected with the second support plate via a second rolling shaft which is parallel to the first horizontal direction.

The connection portion may comprise a fixed frame, a first connecting shaft and a second connecting shaft, the upper clamp portion and the lower clamp portion are located outside of the fixed frame, and the first connecting shaft and the second connecting shaft are located inside of the fixed frame;

a first end of the first connecting shaft is fixed to a middle portion of the second connecting shaft and connected with the fixed frame via a rotary connecting shaft;

a first end of the second connecting shaft is connected with the upper clamp portion via a first connector, and a second end of the second connecting shaft is connected with the lower clamp portion via a second connector; and the fixed frame is provided with a first sliding bore with the first connector therein and a second sliding bore with the second connector therein.

The connection portion may further comprise a cylinder which is connected with a second end of the first connecting shaft and used to drive the first connecting shaft to rotate around the rotary connecting shaft as a rotational shaft.

The guiding clamp may further comprise a horizontal transmission portion which is located between the upper clamp portion and the lower clamp portion and used to contact a side of the flat-panel product so as to drive the flat-panel product to move in the first horizontal direction.

The horizontal transmission portion may comprise a plurality of third rollers arranged in the first horizontal direction and having a rolling shaft parallel to the vertical direction.

When the upper clamp portion and the lower clamp portion are moved toward each other, the minimum distance between the upper clamp portion and the lower clamp portion is in the range of 2.0 mm to 3.5 mm.

The horizontal conveying mechanism may comprise a plurality of elongated rotating shafts, all of which are sequentially disposed in parallel in the first horizontal direction and have a rotating axis parallel to the second horizontal direction; and the elongated rotating shaft is provided with a plurality of transmission wheels that are fixedly connected to the elongated rotating shaft.

The turnover mechanism may comprise a drive wheel, a driven wheel and a turnover rotating shaft, wherein the drive wheel and the driven wheel are connected with each other via a transmission belt, a first end of the turnover rotating shaft is connected with the center of the driven wheel, and a second end of the turnover rotating shaft is connected with the guiding clamp.

The turnover mechanism may further comprise a pressure roller disposed between the drive wheel and the driven wheel, contacting the transmission belt and used to increase acting forces between the transmission belt and the drive wheel and between the transmission belt and the driven wheel.

The turnover mechanism may further comprise a housing which is provided with a retractable projection thereon; and the turnover rotating shaft is provided with a sector engaging member with an edge thereof being in contact with the projection, wherein when the projection is moved to contact a radius edge of the sector engaging member, the projection is engaged with the sector engaging member.

The central angle of the sector engaging member may be 90°.

The flat-panel product inspection device may further comprise a fixed framework, wherein the horizontal conveying mechanism is disposed at the bottom of the fixed framework, and the turnover mechanism and the guiding clamp are disposed on a side of the horizontal conveying mechanism in the second horizontal direction in the fixed framework.

The flat-panel product inspection device may further comprise an illuminating lamp disposed at the top of the fixed framework.

The invention has the following beneficial effects:

The invention provides a flat-panel product inspection device comprising: a horizontal conveying mechanism for driving a flat-panel product in a horizontal state to move in a first horizontal direction; a guiding clamp for clamping the flat-panel product when the flat-panel product is moved to a first position; and a turnover mechanism connected with the guiding clamp and used to drive the guiding clamp to turn around a first rotating axis after the flat-panel product is clamped by the guiding clamp so that the flat-panel product is turned from the horizontal state to a vertical state, the first rotating axis being parallel to the first horizontal direction. With the guiding clamp clamping the flat-panel product, the invention can effectively prevent the problem of "panel drops" from occurring during the process of turning the flat-panel product from the horizontal state to the vertical state. More importantly, after being turned to the vertical state, the to-be-inspected display panel is applied with even forces at both sides, and thus will not deform, thereby guaranteeing that inspection on the flat-panel product can be performed smoothly.

DETAILED DESCRIPTION

Hereinafter, specific embodiments of the disclosure will be described in detail in conjunction with the accompanying drawings. It should be understood that the specific embodiments as set forth herein are merely for the purpose of illustration and explanation of the disclosure and should not be constructed as a limitation thereof.

Figure 1:
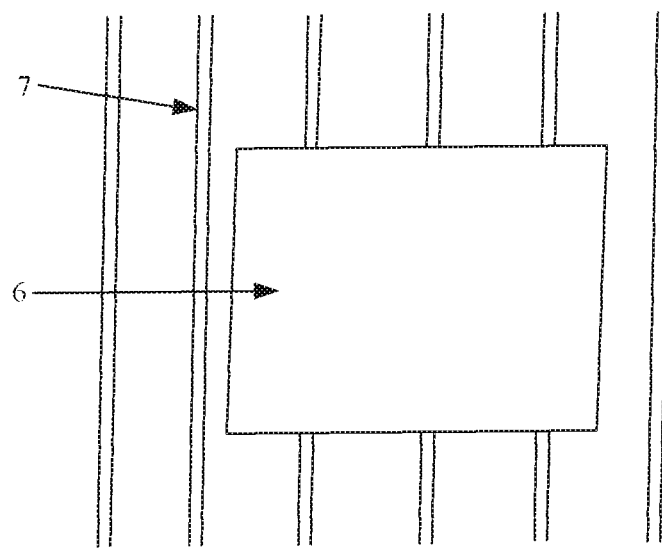
FIG. 1 is a structural schematic diagram of a polarizer visual inspection device in the prior art.
Figure 2:
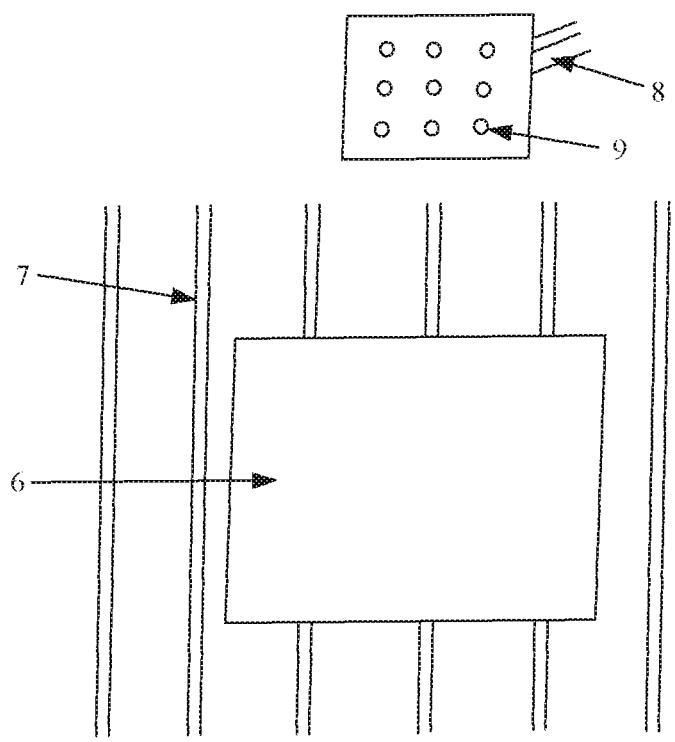
FIG. 2 is a schematic diagram of another polarizer inspection device in the prior art.
Figure 3:
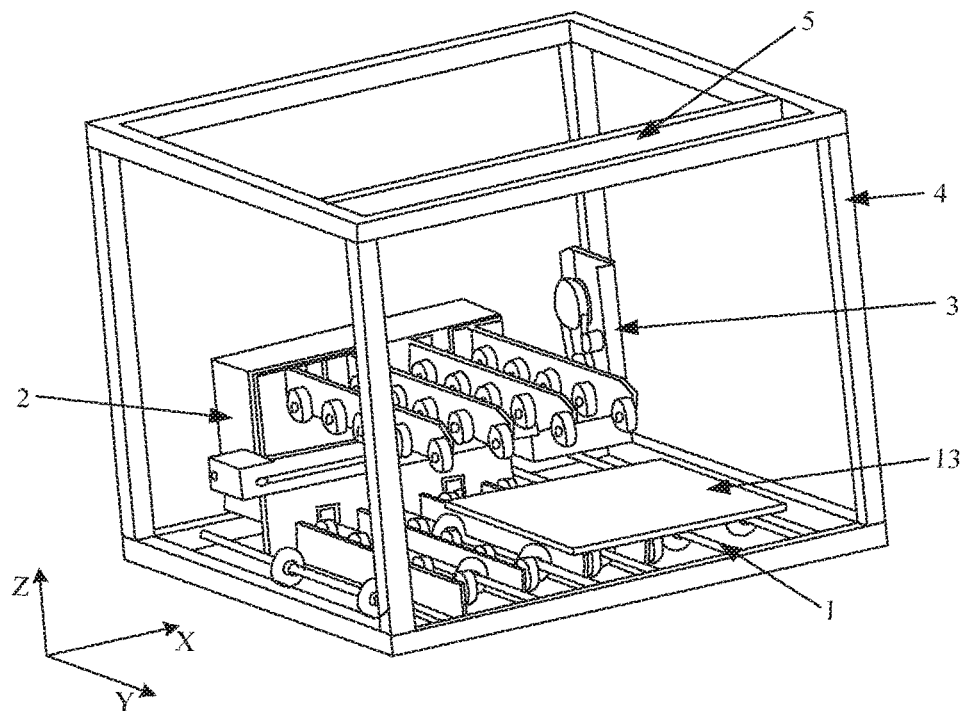
FIG. 3 is a structural schematic diagram of a flat-panel product inspection device according to the exemplary embodiment of the invention.

FIG. 3 is a structural schematic diagram of a flat-panel product inspection device according to the exemplary embodiment of the invention. As shown in FIG. 3, the flat-panel product inspection device comprises: a horizontal conveying mechanism 1 for driving a flat-panel product 13 in a horizontal state to move in a first horizontal direction X; a guiding clamp 2 for clamping the flat-panel product 13 when the flat-panel product 13 is moved to a first position; and a turnover mechanism 3 connected with the guiding clamp 2 and used to drive the guiding clamp 2 to turn around a first rotating axis after the flat-panel product 13 is clamped by the guiding clamp 2 so that the flat-panel product 13 is turned from the horizontal state to a vertical state, the first rotating axis being parallel to the first horizontal direction X.

In this exemplary embodiment, when the turnover mechanism 3 drives guiding clamp 2 to turn so that the flat-panel product 13 is turned to the vertical state, an inspector may perform a corresponding inspection on the flat-panel product 13. For example, when the flat-panel product is a display panel, a polarizer of the display panel in the vertical state on the guiding clamp 2 can be inspected. Compared with the prior art, by clamping the to-be-inspected display panel with the guiding clamp 2, the invention can effectively prevent the problem of "panel drops" from occurring during the process of turning the to-be-inspected display panel from the horizontal state to the vertical state. More importantly, after being turned to the vertical state, the to-be-inspected display panel is applied with even forces at both sides, and thus will not deform, thereby guaranteeing that inspection on the polarizer can be performed smoothly.

It should be noted that the case where the above flat-panel product is a display panel and inspection is perform on the polarizer of the display panel is merely exemplary, which will not limit the technical solution of the invention. The flat-panel product in the invention may be any product having a flat-panel shape, including but not limited to, glass substrate, display substrate, display panel and the like. The specific inspection items can be set according to the actual demands of inspectors.

Figure 4:
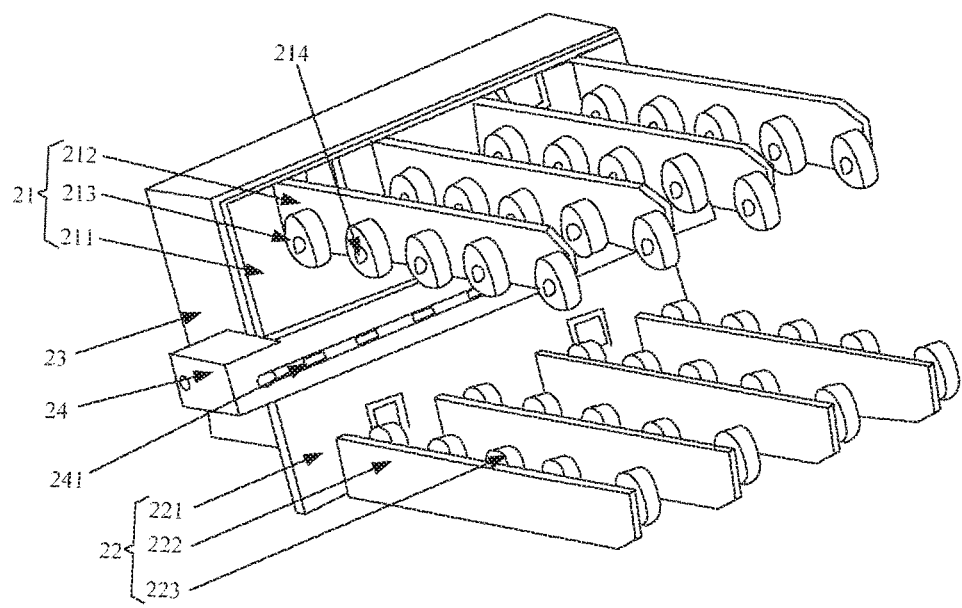
FIG. 4 is a structural schematic diagram of the guiding clamp in FIG. 3.

FIG. 4 is a structural schematic diagram of the guiding clamp 2 in FIG. 3. As shown in FIG. 4, the guiding clamp 2 comprises an upper clamp portion 21, a lower clamp portion 22 and a connection portion 23 connected with the upper clamp portion 21 and the lower clamp portion 22, the upper clamp portion 21 and the lower clamp portion 22 being provided to be parallel to each other; and the connection portion 23 is used to drive the upper clamp portion 21 and the lower clamp portion 22 to move toward or away from each other in a vertical direction Z. Specifically, when the guiding clamp 2 is provided at the first position, and the guiding clamp 2 is in an initial state, a distance between the upper clamp portion 21 and the lower clamp portion 22 is maximum (which can be designed according to actual demands). At this time, the lower clamp portion 22 is located below the flat-panel product 13, and the upper clamp portion 21 is located above the flat-panel product 13. During clamping, the connection portion 23 drives the upper clamp portion 21 to move vertically downwards and drives the lower clamp portion 22 to move vertically upwards, until the distance between the upper clamp portion 21 and the lower clamp portion 22 is minimum. In such case, the upper clamp portion 21 and the lower clamp portion 22 cooperate with each other to clamp the flat-panel product 13.

In this exemplary embodiment; in order to ensure that the flat-panel product 13 can be clamped by the upper clamp portion 21 and the lower clamp portion 22 and will not deform due to extrusion caused by excessive clamping force, the minimum distance between the upper clamp portion 21 and the lower clamp portion 22 is preferably in the range of 2.0 mm to 3.5 mm. Obviously, in practical applications, the minimum distance may be adjusted according to the actual thickness of the flat-panel product 13.

As a specific embodiment, the upper clamp portion 21 comprises a first connection plate 211 and a plurality of first support plates 212 which are sequentially arranged in the first horizontal direction X, and all of the first support plates 212 are parallel to each other and extend along a second horizontal direction Y; and the lower clamp portion 22 comprises a second connection plate 221 and a plurality of second support plates 222 which are sequentially arranged in the first horizontal direction X, and all of the second support plates 222 are parallel to each other and extend along the second horizontal direction Y. When turned to the vertical state, the flat-panel product 13 can be inspected by inspectors through gaps between the second support plates 222.

Alternatively, a side of the first support plate 212 is provided with a plurality of first rollers 213 that are connected with the first support plate 212 via a first rolling shaft 214 which is parallel to the first horizontal direction X; and a side of the second support plate 222 is provided with a plurality of second rollers 223 that are connected with the second support plate 222 via a second rolling shaft (not shown) which is parallel to the first horizontal direction X. After the flat-panel product 13 is clamped, the position of the flat-panel product 13 in the second horizontal direction Y is adjusted accordingly by controlling the first rollers 213 and the second rollers 223 to rotate.

It should be noted that when the first support plate 212 is provided with the first rollers 213 on the side and the second support plates 222 is provided with the second rollers 223 on the side, the acting forces between the upper and lower clamp portions 21, 22 and the flat-panel product 13 are point acting forces, namely, the acting areas are small, which can effectively reduce the risk of causing defects of the flat-panel product 13 by the guiding clamp 2.

Alternatively, the guiding clamp 2 further comprises a horizontal transmission portion 24 which is located between the upper clamp portion 21 and the lower clamp portion 22 and used to contact a side of the flat-panel product 13 so as to drive the flat-panel product 13 to move in the first horizontal direction X. Specifically, the horizontal transmission portion 24 comprises a plurality of third rollers 241 arranged in the first horizontal direction X and having a rolling shaft parallel to the vertical direction Z, and after the flat-panel product 13 is clamped, the position of the flat-panel product 13 in the first horizontal direction X can be adjusted by the third rollers 241 of the horizontal transmission portion 24.

Figure 5:
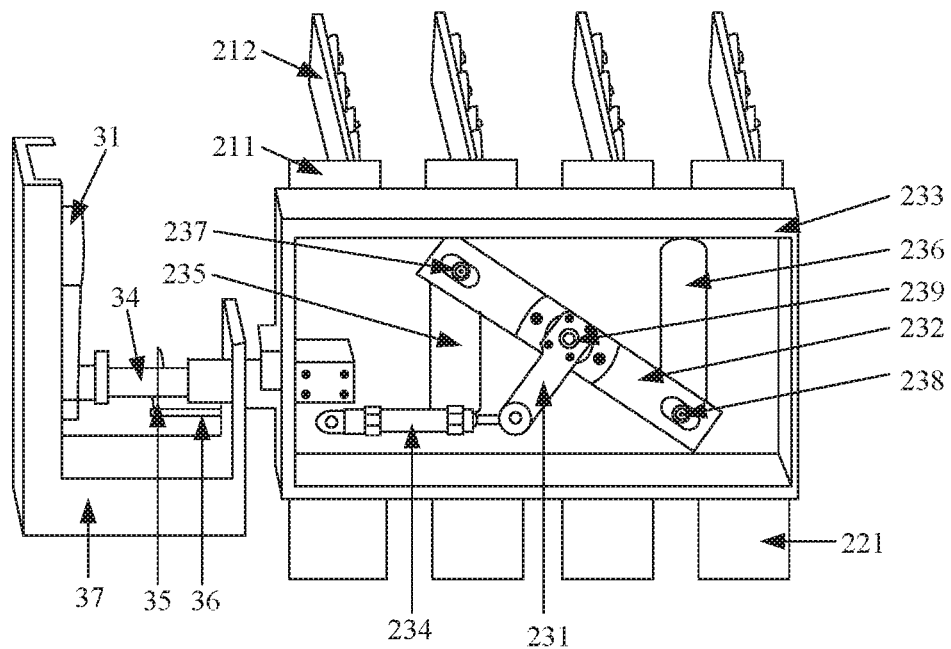
FIG. 5 is a schematic diagram illustrating a connection state of the turnover mechanism and the guiding clamp in FIG. 3.

FIG. 5 is a schematic diagram illustrating a connection state of the turnover mechanism 3 and the guiding clamp 2 in FIG. 3. As shown in FIG. 5, the connection portion 23 of the guiding clamp 2 comprises a fixed frame 233, a first connecting shaft 231 and a second connecting shaft 232, wherein the upper clamp portion 21 and the lower clamp portion 22 are located outside of the fixed frame 233, and the first connecting shaft 231 and the second connecting shaft 232 are located inside of the fixed frame 233; a first end of the first connecting shaft 231 is fixed to a middle portion of the second connecting shaft 232 and connected with the fixed frame 233 via a rotary connecting shaft 239; a first end of the second connecting shaft 232 is connected with the upper clamp portion 21 via a first connector 237, and a second end of the second connecting shaft 232 is connected with the lower clamp portion 22 via a second connector 238; and the fixed frame 233 is provided with a first sliding bore 235 with the first connector 237 therein and a second sliding bore 236 with the second connector 238 therein.

Taking the case shown in FIG. 5 as an example, when the first connecting shaft 231 drives the second connecting shaft 232 to rotate in a counterclockwise direction, the upper clamp portion 21 is moved vertically downwards, and the lower clamp portion 22 is moved vertically upwards, thereby the flat-panel product 13 is clamped; when the first connecting shaft 231 drives the second connecting shaft 232 to rotate in a clockwise direction, the upper clamp portion 21 is moved vertically upwards, and the lower clamp portion 22 is moved vertically downwards, thereby the flat-panel product 13 may be placed on the horizontal conveying mechanism 1.

Alternatively, the connection portion 23 further comprises a cylinder 234 which is connected with a second end of the first connecting shaft 231 and used to drive the first connecting shaft 231 to rotate around the rotary connecting shaft 239 as a rotational shaft, thereby realizing the guiding clamp 2 switched between an initial state and a clamping state.

Figure 6:
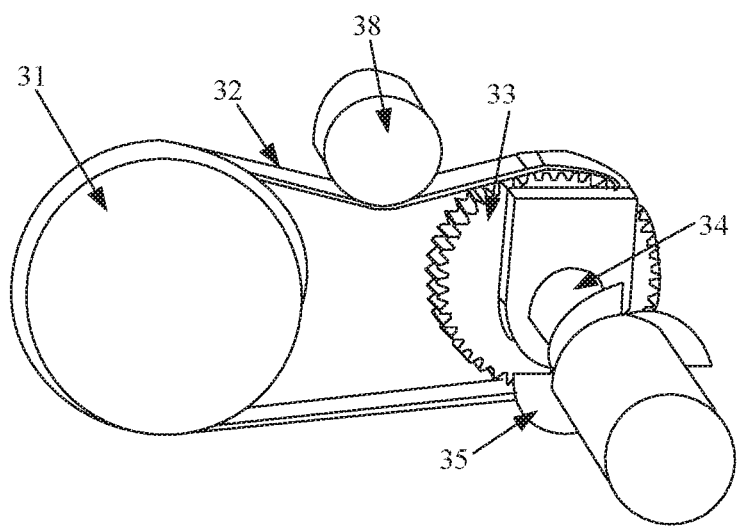
FIG. 6 is a structural schematic diagram of the turnover mechanism in FIG. 3.

FIG. 6 is a structural schematic diagram of the turnover mechanism 3 in FIG. 3. As shown in FIG. 6, the turnover mechanism 3 comprises a drive wheel 31, a driven wheel 33 and a turnover rotating shaft 34, wherein the drive wheel 31 and the driven wheel 33 are connected with each other via a transmission belt 32, a first end of the turnover rotating shaft 34 is connected with the center of the driven wheel 33, and a second end of the turnover rotating shaft 34 is connected with the guiding clamp 2. When the drive wheel 31 drives the driven wheel 33 to rotate via the transmission belt 32, the turnover rotating shaft 34 is rotated accordingly so as to drive the guiding clamp 2 to turn.

Alternatively, the turnover mechanism 3 further comprises a pressure roller 38 disposed between the drive wheel 31 and the driven wheel 33, contacting the transmission belt 32 and used to increase acting forces between the transmission belt 32 and the drive wheel 31 and between the transmission belt 32 and the driven wheel 33, thereby preventing slipping from between the transmission belt 32 and the drive wheel 31 and between the transmission belt 32 and the driven wheel 33.

Alternatively, the turnover mechanism 3 further comprises a housing 37 which is provided with a retractable projection 36 thereon. The turnover rotating shaft 34 is provided with a sector engaging member 35 with an edge thereof being in contact with the projection 36. When the projection 36 is moved to a position where it contacts a radius edge of the sector engaging member 35, the projection 36 is engaged with the sector engaging member 35. In this exemplary embodiment, by providing the retractable projection 36 and the sector engaging member 35, it is possible to accurately control the extent of rotation of the guiding clamp 2. Further, the central angle of the sector engaging member 35 is 90°, thereby achieving a rotational movement of 90° of the turnover mechanism 3, i.e., it is possible to switch the guiding clamp 2 between a horizontal state and a vertical state, which can help inspectors perform an inspection on the flat-panel product 13. It should be rioted that the invention is not limited thereto, the central angle of the sector engaging member 35 may be any angle from 0° to 180°, but in order to facilitate the inspection by inspectors, the central angle of the sector engaging member 35 is preferably 60°, 90° or 120°.

Figure 7:
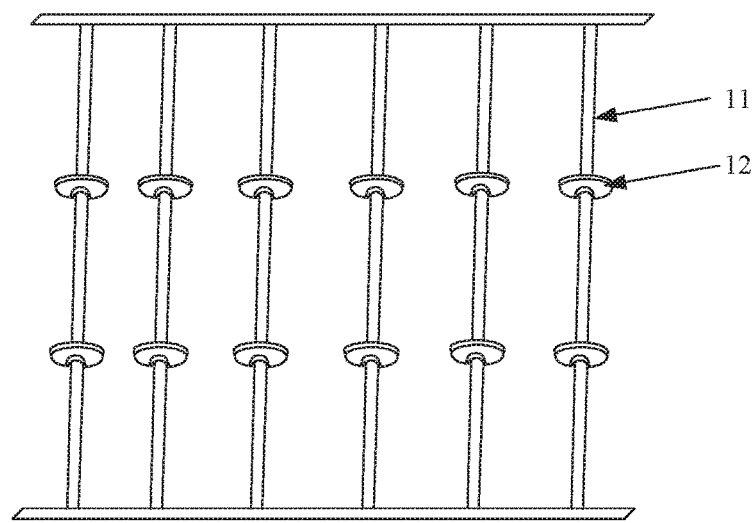
FIG. 7 is a structural schematic diagram of the horizontal conveying mechanism in FIG. 3.

FIG. 7 is a structural schematic diagram of the horizontal conveying mechanism in FIG. 3. As shown in FIG. 7, the horizontal conveying mechanism 1 comprises a plurality of elongated rotating shafts 11, all of which are sequentially disposed in parallel in the first horizontal direction and have a rotating axis parallel to the second horizontal direction Y. When the elongated rotating shafts 11 rotate, the flat-panel product 13 may be driven to move horizontally in the first horizontal direction X.

Alternatively, the elongated rotating shaft 11 is provided with a plurality of transmission wheels 12 that are fixedly connected to the elongated rotating shaft 11. At this time, the acting forces between the transmission wheels 12 and the flat-panel product 13 are point acting forces, namely, the acting areas are small, which can effectively reduce defects of the flat-panel product 13 caused by the horizontal conveying mechanism 1.

The working process of the flat-panel product inspection device according to the exemplary embodiment will be described in detail below in conjunction with FIGS. 8-10.

Figure 8:
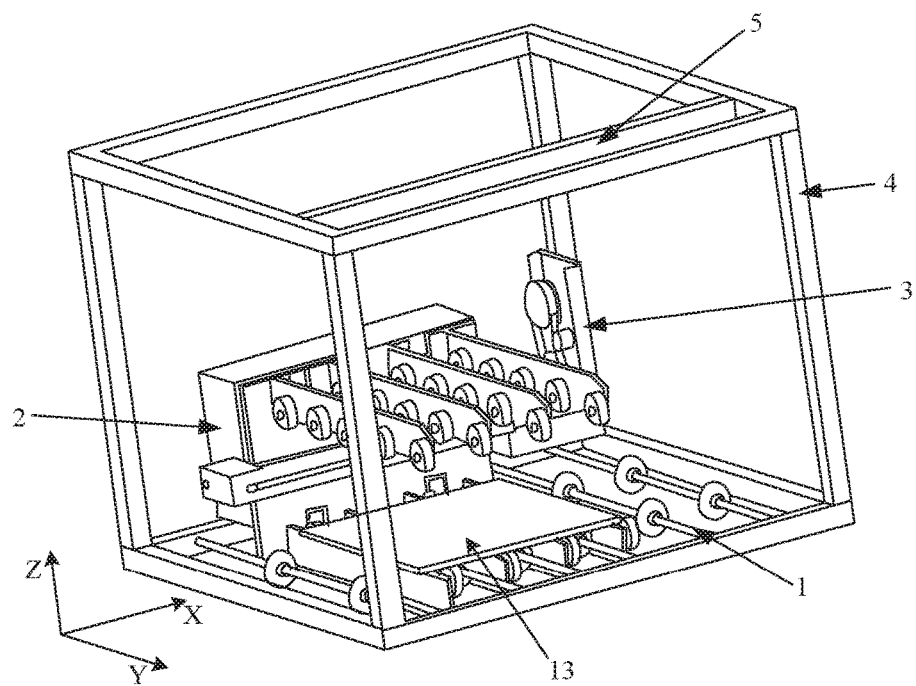
FIG. 8 is a schematic diagram illustrating the flat-panel product moved to a first position.

FIG. 8 is a schematic diagram illustrating the flat-panel product 13 moved to a first position. As shown in FIG. 8, the cylinder 234 is in a closed state, the guiding clamp 2 is in an initial state, the upper clamp portion 21 is located above the first position, and the lower clamp portion 22 is located below the first position. The horizontal conveying mechanism 1 drives the flat-panel product 13 to move horizontally in the first horizontal direction X, and when the flat-panel product 13 is moved to the first position, the horizontal conveying mechanism 1 is stopped.

Figure 9:
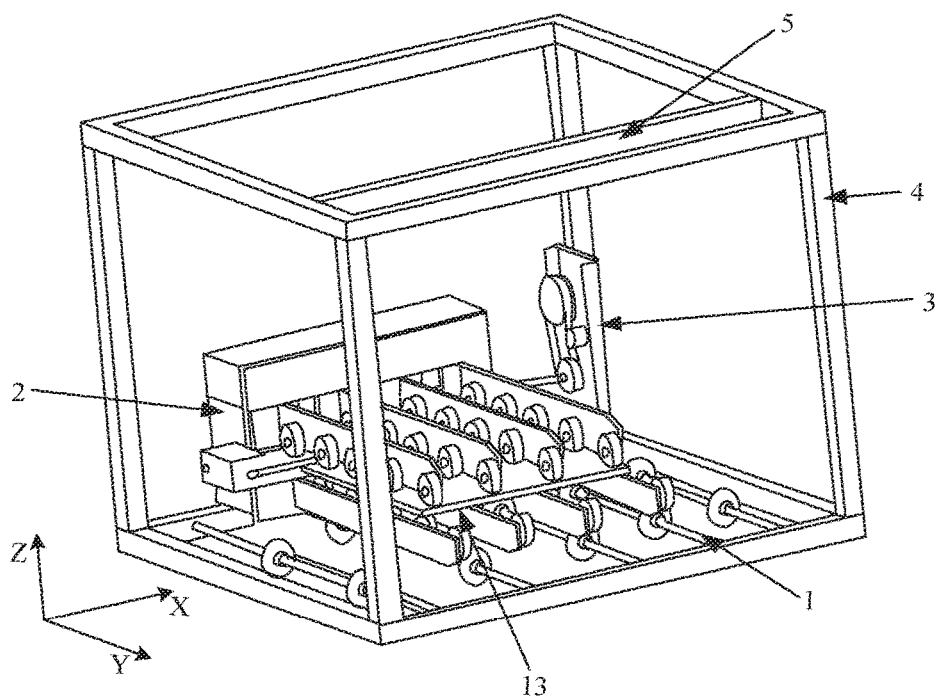
FIG. 9 is a schematic diagram illustrating the guiding clamp clamping the flat-panel product.

FIG. 9 is a schematic diagram illustrating the guiding clamp 2 clamping the flat-panel product 13. As shown in FIG. 9, the cylinder 234 is switched from the closed state to an open state so as to drive the first connecting shaft 231 to rotate in the counterclockwise direction. At this time, the second connecting shaft 232 is rotated synchronously in the counterclockwise direction. In such case, the first connection plate 211 and the first support plates 212 are moved vertically downwards, and the second connection plate 221 and the second support plates 222 are moved vertically upwards, and when the first support plates 212 and the second support plates 222 are moved relatively to a position at which the distance therebetween is minimum, the flat-panel product 13 is clamped.

If the inspectors found that the side of the flat-panel product 13 is not in contact with the third rollers 241, the first rollers 213 and the second rollers 223 can be controlled to rotate, so as to drive the flat-panel product 13 to move in the second horizontal direction Y until the side of the flat-panel product 13 is in contact with the third rollers 241.

Figure 10:
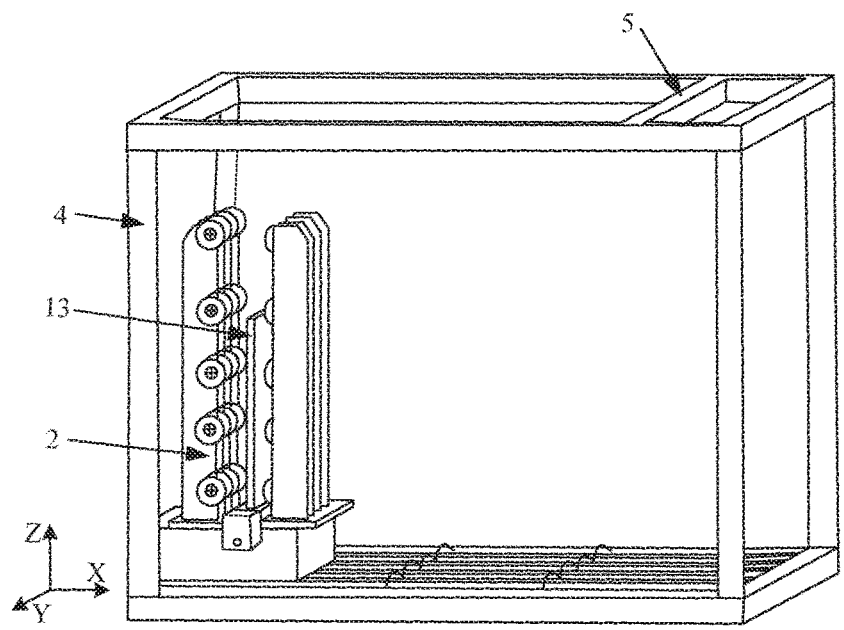
FIG. 10 is a schematic diagram illustrating the guiding clamp and the flat-panel product turned to a vertical state by the turnover mechanism.

FIG. 10 is a schematic diagram illustrating the guiding clamp 2 and the flat-panel product 13 turned to a vertical state by the turnover mechanism. As shown in FIG. 10, the drive wheel 31 drives the driven wheel 33 to rotate in the counterclockwise direction. At this time, the turnover rotating shaft 34 (which is in the same line with the first rotating axis) is rotated synchronously so as to drive the guiding clamp 2 to rotate accordingly. The sector engaging member 35 is engaged with the projection 36 after the turnover rotating shaft 34 is rotated 90°. At this time, the drive wheel 31 stops. Accordingly, the guiding clamp 2 and the flat-panel product 13 are moved from the horizontal state to the vertical state. At this time, the inspectors may conduct corresponding inspection on the flat-panel product 13.

During the inspection by the inspectors, part of the region on the flat-panel product 13 is shielded by the second support plates 222 and the second rollers 223. In such case, the third rollers 241 is controlled to rotate so as to drive the flat-panel product 13 to move in the first horizontal direction X, thereby facilitating the inspection on the region shielded by the second support plates 222 and the second rollers 223 by the inspectors.

It should be noted that when the inspectors inspect the flat-panel product 13 on the horizontal conveying mechanism 1 in a "sampling inspection" manner, during the corresponding inspection on the sampled flat-panel product 13 by the inspectors, the horizontal conveying mechanism 1 may re-start working again so as to convey the other flat-panel products 13 which are not sampled, thereby improving production efficiency.

When the inspectors complete the inspection, the horizontal conveying mechanism 1 is firstly stopped; then the projection 36 is controlled to contract, and the drive wheel 31 in the turnover mechanism 3 is driven to rotate in a clockwise direction, so that the guiding clamp 2 and the flat-panel product 13 are moved from the vertical state to the horizontal state; subsequently, the first rollers 213 and the second rollers 223 are controlled to rotate so as to drive the flat-panel product 13 to move in the second horizontal direction Y until the flat-panel product 13 is located directly above the first position; and finally, the cylinder 234 is switched from the open state to the closed state so as to drive the first connecting shaft 231 to rotate in the clockwise direction. At this time, the second connecting shaft 232 is rotated synchronously in the clockwise direction. In such case, the first connection plate 211 and the first support plates 212 are moved vertically upwards and the second connection plate 221 and the second support plates 222 are moved vertically downwards until the guiding clamp 2 is in the initial state. During this process, the flat-panel product 13 located on the second support plates 222 is placed at the first position on the horizontal conveying mechanism 1.

It should be noted that the case that where the above drive wheel 31 drives the driven wheel 33 to rotate in the counterclockwise direction so as to change move the flat-panel product 13 from the horizontal state to the vertical state is merely exemplary, which will not limit the technical solution of the invention. Those skilled in the art should understand that, in the invention, by changing the relative positions of the turnover mechanism 3 and the guiding clamp 2, the flat-panel product 13 can may be changed moved from the horizontal state to the vertical state when the drive wheel 31 drives the driven wheel 33 to rotate in the clockwise direction.

Alternatively, the flat-panel product inspection device further comprises a fixed framework 4, wherein the horizontal conveying mechanism 1 is disposed at the bottom of the fixed framework 4, and the turnover mechanism 3 and the guiding clamp 2 are disposed on the side of the horizontal conveying mechanism 1 in the second horizontal direction Y in the fixed framework 4. In this exemplary embodiment, the horizontal conveying mechanism 1, the turnover mechanism 3 and the guiding clamp 2 are integrally held together by the fixed framework 4, thus facilitating the overall movement and assembly of the flat-panel product inspection device.

Alternatively, the flat-panel product inspection device further comprises an illuminating lamp 5 which is disposed at the top of the fixed framework 4 and provides a suitable light source during inspection on the flat-panel product by inspectors.

It should be understood that the above embodiments are merely exemplary embodiments for the purpose of illustrating the principle of the disclosure, and the disclosure is not limited thereto. Various modifications and improvements can be made by a person having ordinary skill in the art without departing from the spirit and essence of the disclosure. Accordingly, all of the modifications and improvements also fall into the protection scope of the disclosure.

What is claimed is:

1. A flat-panel product inspection device comprising:
   a horizontal conveying mechanism for driving a flat-panel product in a horizontal state to move in a first horizontal direction;
   a guiding clamp for clamping the flat-panel product when the flat-panel product is moved to a first position; and
   a turnover mechanism connected with the guiding clamp and used to drive the guiding clamp to turn around a first rotating axis after the flat-panel product is clamped by the guiding clamp, so that the flat-panel product is turned from the horizontal state to a vertical state, the first rotating axis being parallel to the first horizontal direction;
   wherein the guiding clamp comprises an upper clamp portion, a lower clamp portion and a connection portion connected with the upper clamp portion and the lower clamp portion, and the upper clamp portion and the lower clamp portion are provided to be parallel to each other; and
   wherein the connection portion is used to drive the upper clamp portion and the lower clamp portion to move toward or away from each other in a vertical direction.

2. The flat-panel product inspection device according to claim 1,
   wherein the upper clamp portion comprises a first connection plate and a plurality of first support plates which are sequentially arranged in the first horizontal direction, and all of the first support plates are parallel to each other and extend along a second horizontal direction; and
   wherein the lower clamp portion comprises a second connection plate and a plurality of second support plates which are sequentially arranged in the first horizontal direction, and all of the second support plates are parallel to each other and extend along the second horizontal direction.

3. The flat-panel product inspection device according to claim 2,
   wherein a side of the first support plate is provided with a plurality of first rollers that are connected with the first support plate via a first rolling shaft which is parallel to the first horizontal direction; and
   wherein a side of the second support plate is provided with a plurality of second rollers that are connected with the second support plate via a second rolling shaft which is parallel to the first horizontal direction.

4. The flat-panel product inspection device according to claim 1,
   wherein the connection portion comprises a fixed frame, a first connecting shaft and a second connecting shaft, the upper clamp portion and the lower clamp portion are located outside of the fixed frame, and the first connecting shaft and the second connecting shaft are located inside of the fixed frame;
   wherein a first end of the first connecting shaft is fixed to a middle portion of the second connecting shaft and connected with the fixed frame via a rotary connecting shaft;
   wherein a first end of the second connecting shaft is connected with the upper clamp portion via a first connector, and a second end of the second connecting shaft is connected with the lower clamp portion via a second connector; and
   wherein the fixed frame is provided with a first sliding bore with the first connector therein and a second sliding bore with the second connector therein.

5. The flat-panel product inspection device according to claim 4,
   wherein the connection portion further comprises a cylinder which is connected with a second end of the first connecting shaft and used to drive the first connecting shaft to rotate around the rotary connecting shaft as a rotational shaft.

6. The flat-panel product inspection device according to claim 1,
wherein the guiding clamp further comprises a horizontal transmission portion which is located between the upper clamp portion and the lower clamp portion and used to contact a side of the flat-panel product so as to drive the flat-panel product to move in the first horizontal direction.

7. The flat-panel product inspection device according to claim 6,
wherein the horizontal transmission portion comprises a plurality of third rollers arranged in the first horizontal direction and having a rolling shaft parallel to the vertical direction.

8. The flat-panel product inspection device according to claim 1,
wherein when the upper clamp portion and the lower clamp portion are moved toward each other, the minimum distance between the upper clamp portion and the lower clamp portion is in the range of 2.0 mm to 3.5 mm.

9. The flat-panel product inspection device according to claim 1,
wherein the horizontal conveying mechanism comprises a plurality of elongated rotating shafts, all of which are sequentially disposed in parallel in the first horizontal direction and have a rotating axis parallel to the second horizontal direction; and
wherein the elongated rotating shaft is provided with a plurality of transmission wheels that are fixedly connected to the elongated rotating shaft.

10. The flat-panel product inspection device according to claim 1,
wherein the turnover mechanism comprises a drive wheel, a driven wheel and a turnover rotating shaft, the drive wheel and the driven wheel are connected with each other via a transmission belt, a first end of the turnover rotating shaft is connected with the center of the driven wheel, and a second end of the turnover rotating shaft is connected with the guiding clamp.

11. The flat-panel product inspection device according to claim 10,
wherein the turnover mechanism further comprises a pressure roller disposed between the drive wheel and the driven wheel, contacting the transmission belt and used to increase acting forces between the transmission belt and the drive wheel and between the transmission belt and the driven wheel.

12. The flat-panel product inspection device according to claim 10,
wherein the turnover mechanism further comprises a housing which is provided with a retractable projection thereon; and
wherein the turnover rotating shaft is provided with a sector engaging member with an edge thereof being in contact with the projection, and when the projection is moved to contact a radius edge of the sector engaging member, the projection is engaged with the sector engaging member.

13. The flat-panel product inspection device according to claim 12,
wherein the central angle of the sector engaging member is 90°.

14. The flat-panel product inspection device according to claim 1, further comprising a fixed framework, wherein the horizontal conveying mechanism is disposed at the bottom of the fixed framework, and the turnover mechanism and the guiding clamp are disposed on a side of the horizontal conveying mechanism in the second horizontal direction in the fixed framework.

15. The flat-panel product inspection device according to claim 14, further comprising an illuminating lamp disposed at the top of the fixed framework.

* * * * *